United States Patent [19]

Wang

[11] Patent Number: 5,088,480
[45] Date of Patent: Feb. 18, 1992

[54] LOWER LEG ORTHOSIS APPARATUS

[76] Inventor: Tzu C. Wang, 1446 Sugar Creek Blvd., Sugar Land, Tex. 77478

[21] Appl. No.: 401,886

[22] Filed: Sep. 1, 1989

[51] Int. Cl.⁵ .................................................. A61F 5/00
[52] U.S. Cl. ........................... 602/23; 128/80 E; 128/80 H; 128/83.5; 128/87 R
[58] Field of Search ............... 128/80 D, 80 R, 80 E, 128/80 F, 80 H, 80 J, 83 R, 83.5, 84 R, 87 R

[56] References Cited

U.S. PATENT DOCUMENTS

| | | | |
|---|---|---|---|
| 3,606,884 | 9/1971 | Peter | 128/80 E |
| 3,713,437 | 1/1973 | Wiedmer | 128/80 E |
| 3,805,773 | 4/1974 | Sichau | 128/80 E |
| 4,102,337 | 7/1978 | Gola | 128/80 E |
| 4,289,122 | 9/1981 | Mason et al. | 128/80 E |
| 4,554,912 | 11/1985 | Haberman | 128/80 E |
| 4,651,723 | 3/1987 | Satoh | 128/80 E |

Primary Examiner—Edgar S. Burr
Assistant Examiner—Moshe I. Cohen
Attorney, Agent, or Firm—Henderson & Sturm

[57] ABSTRACT

An adjustable and re-usable lower leg orthosis apparatus (10) including a calf unit (11) and a foot unit (12) adjustably connected to one another by a connector brace unit (13) to accommodate patients having different leg and calf configurations.

5 Claims, 1 Drawing Sheet

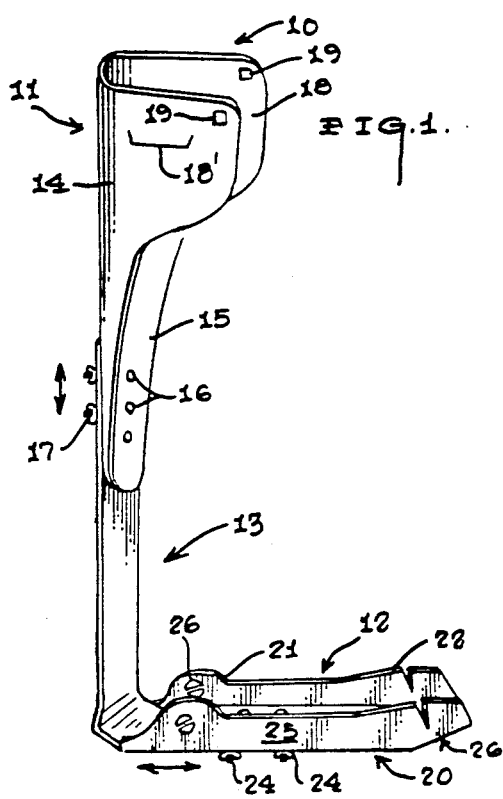
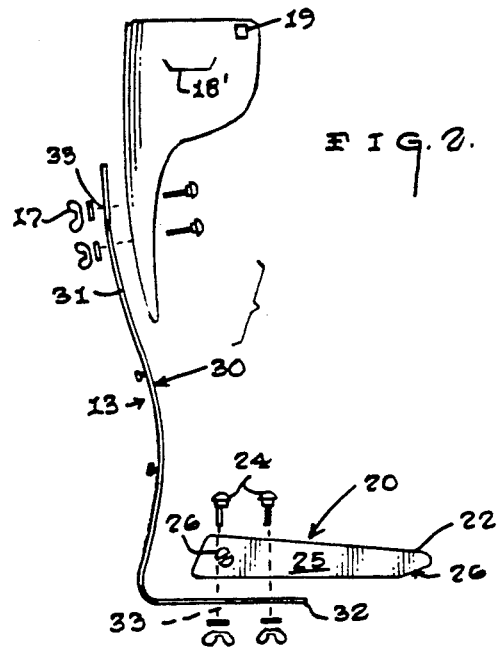
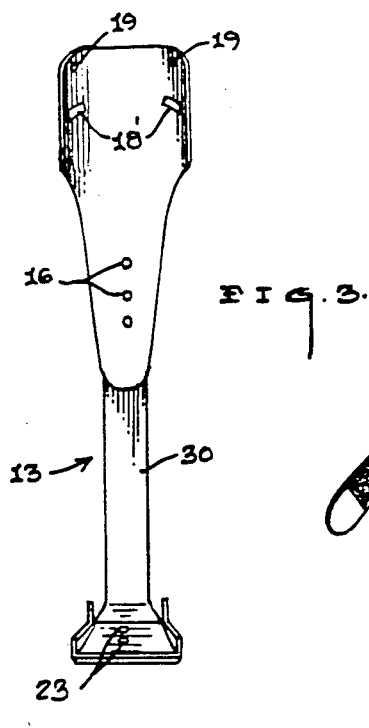
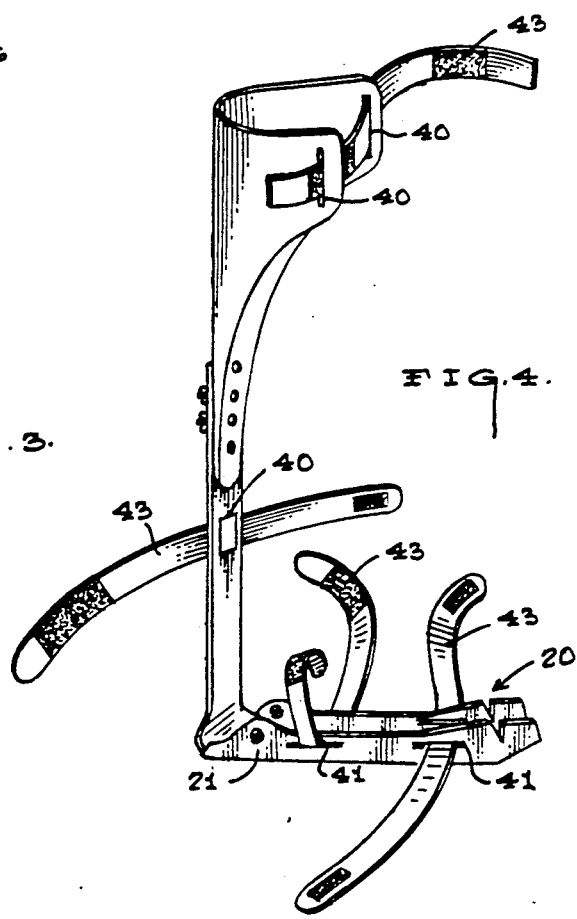

LOWER LEG ORTHOSIS APPARATUS

TECHNICAL FIELD

This invention relates in general to leg brace device, and in particular to leg brace devices for the lower part of the leg.

BACKGROUND OF THE INVENTION

This invention was the subject matter of Document Disclosure Program Registration Number 224035 which was filed in the U.S. Patent and Trademark Office on Apr. 10, 1989.

As can be seen by reference to the following U.S. Pat. Nos.: 3,606,884; 4,289,122; 4,554,912; and 4,102,337 the prior art is replete with myriad and diverse lower leg orthosis.

While the prior art constructions are more than adequate for the basic purpose and function for which they were specifically designed, they do suffer from a number of shared deficiencies.

For instance, most of the prior art constructions lack an adjustment feature to compensate for the re-use of the lower leg device by different sized individuals. The prior art constructions are also designed to be molded or built to accommodate a specific foot and only that foot.

This particular deficiency makes the likelihood of re-use of the device extremely unlikely; thereby, creating a large one time expense for the user of the leg splint.

In addition, another common deficiency in the prior art constructions involves the fact that there is no place to attach a wrapping or bandage to the lower leg orthosis apparatus which causes an irritation for the user by making it possible for the bandage to slide down the user's leg. This also causes the bandage and lower leg orthosis apparatus to act as separate units which is not a desirable feature.

It should also be noted that some of the prior art constructions do not possess the characteristics of being durable and lightweight at the same time.

Obviously, there has been a longstanding need for a lower leg orthosis apparatus which incorporates the features of flexibility, adjustability, and durability; and, the development of such a device is a stated objective of the present invention.

SUMMARY OF THE INVENTION

The lower leg orthosis apparatus that forms the basis of the present invention comprises in general: a calf unit; a foot unit; and a connection bar unit.

The calf unit comprises in general: a calf support member wherein the calf support member has a plurality of aligned apertures for the selective accommodate of a first set of fasteners. By changing the choice of the particular apertures used to install the fasteners permits the calf unit to be vertically adjustable to accommodate different sized calves.

The calf unit also has two elongated slits formed in its upper portion to allow a bandage or wrap to be used in conjunction with the apparatus. This arrangement will insure that the bandage will not be able to slide down the user's leg as is the case with many of the prior art constructions.

The foot unit comprises in general: a foot support base member provided with a plurality of aligned apertures to accommodate a second set of fasteners. As was the case with the calf unit, the choosing of the particular apertures to insert the fastener enables the foot unit to accommodate different sized feet.

In addition, the heel portion of the support base member is provided with a plurality of holes which can be used for leg traction purposes; and, the toe portion of the support base member is provided with a wedge shaped portion to accommodate the user's toes.

The connection bar unit joins the calf and the foot units together and also serves as a durable and rigid support member. The connection bar unit also is provided with a plurality of apertures formed on each end for receiving the foot and calf fasteners.

Briefly stated, the aforementioned apparatus allows different sized feet and calves to be protectively supported by a single versatile lower leg orthosis apparatus which can accommodate a variety of patients.

BRIEF DESCRIPTION OF THE DRAWINGS

These and other objects, advantages and novel features of the invention will become more apparent from the detailed description of the best mode for carrying out the preferred embodiment of this invention which follows; particularly when considered in conjunction with the accompanying drawings, wherein:

FIG. 1 is a perspective view of the preferred embodiment of the invention;

FIG. 2 is an exploded perspective view of the apparatus;

FIG. 3 is a front view of the apparatus; and,

FIG. 4 is a perspective view of an alternate embodiment of the invention.

BEST MODE FOR CARRYING OUT THE INVENTION

As can best be seen by reference to the drawings and in particular to FIG. 1, the lower leg orthosis apparatus of this invention is designated generally by the reference numeral (10). The apparatus (10) comprises in general: a calf unit (11); a foot unit (12); and a connector brace unit (13). These units will now be described in seriatim fashion.

As can be seen by reference to FIGS. 1 and 2, the calf unit (11) comprises a generally rounded contoured calf-shaped calf support member (14) wherein the lower portion (15) of the calf support member (14) is provided with a plurality of vertically aligned mounting apertures (16) designed to receive a first set of standard fastener (17). The upper portion (18) of the calf support member (14) is further provided with two relatively elongated generally U-shaped slits (18') for the purpose of captively receiving a conventional elastic bandage (not shown). This allows the user to securely fasten the bandage to the calf unit (11). Furthermore, the upper portion (18) of the calf support member (14) is also provided with a pair of generally square holes (19) which can be engaged by a conventional knee immobilization device (not shown).

Referring now to FIGS. 1 thru 3, it can be seen that the foot unit (12) comprises a foot base support member (20) comprising a heel (21) and toe portion (22) wherein the heel portion (21) is provided with a plurality of horizontally aligned mounting apertures (23) designed to receive a second set of standard fasteners (24). The choice of the particular apertures (23) in which to install the fasteners (24) gives the foot unit (12) the ability to accommodate different sized feet.

The heel portion (21) of the base support member (20) is further provided with raised side walls (25) having opposed traction hook holes (26) which can be attached to a conventional leg traction device (not shown). In addition, the toe portion (22) of the base support member (20) is provided with a raised lip (26) which is bent upwardly to more readily accommodate the user's toes in a more natural position.

Still referring to FIGS. 1 and 2, it can be seen that the connector brace unit (13) comprises an elongated generally L-shaped connector member (30) wherein the leg (31) and the foot (32) portions of the connector member (30) are provided with a plurality of mounting apertures (33) which are dimensioned to receive the first (17) and second (24) sets of standard fasteners for operatively and selectively engaging the calf unit (11) and the foot unit (12) to the connection bar unit (13) in a well recognized fashion.

In the alternate embodiment of the invention depicted in FIG. 4 it can be seen that both the upper portion (18) of the calf support member (14) and the intermediate portion of the connector member (30) are provided with opposed vertical slots (40); while the side walls (25) of the heel portion (21) of the base support member (20) are provided with opposed horizontal slots (41). In addition, the horizontal (41) and vertical (40) slots are dimensioned to receive fastening straps (43) for use in instances wherein conventional elastic bandaging is not desirable.

At this juncture it should be appreciated that the apparatus (10) as herein described is adjustable in both the horizontal and vertical planes to accommodate different foot and calf configurations; wherein, this single apparatus can be re-used numerous times for different patients, thereby lowering the health care costs for all those individuals that suffer an injury which causes them to wear this type of apparatus.

Having thereby described the subject matter of this invention it should be apparent that many substitutions, modifications, and variations of the invention are possible in light of the above teachings. It is therefore to be understood that the invention as taught and described herein is only to be limited by the breadth and scope of the appended claims.

I claim:

1. An adjustable lower leg orthosis apparatus for patients having different foot and calf configurations wherein the apparatus consisting of:
   a calf unit including a rounded contoured calf support member having a lower portion provided with a plurality of vertically aligned mounting apertures;
   a foot unit including a base support member having a heel portion and a toe portion wherein the heel portion is provided with a plurality of horizontally aligned mounting apertures;
   a connector brace unit consisting of a single generally L-shaped connector member having apertured foot and leg portions;
   a first and second set of standard fasteners for operatively, selectively and adjustably engaging the calf unit and the foot unit to the connector brace unit to accommodate different length feet and different height calves; and,
   at least one fastening strap associated with the calf unit, the foot unit; and the connector brace unit for securing the orthosis apparatus to the users lower leg.

2. The apparatus as in claim 1 wherein the calf support member is also provided with an upper portion having a plurality of generally U-shaped opposed slits; and, a pair of opposed holes.

3. The apparatus as in claim 1 wherein the calf support member is further provided with an upper portion having a plurality of vertically disposed slots which are dimensioned to receive fastening straps.

4. The apparatus as in claim 3 wherein the base support member is provided with a plurality of horizontally disposed slots which are dimensioned to receive fastening straps; and, wherein the leg portion of the connector member is provided with a plurality of vertically disposed slots which are dimensioned to receive fastening straps.

5. The apparatus as in claim 1 wherein the toe portion of the base support member is provided with an upwardly raised lip.

* * * * *